United States Patent
Regensburger

(10) Patent No.: US 12,080,405 B2
(45) Date of Patent: Sep. 3, 2024

(54) METHOD FOR CREATING A THREE-DIMENSIONAL MEDICAL IMAGE

(71) Applicant: Siemens Healthcare GmbH, Erlangen (DE)

(72) Inventor: Alois Regensburger, Poxdorf (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 124 days.

(21) Appl. No.: 17/971,759

(22) Filed: Oct. 24, 2022

(65) Prior Publication Data

US 2023/0129687 A1 Apr. 27, 2023

(30) Foreign Application Priority Data

Oct. 27, 2021 (DE) ...................... 10 2021 212 141.1

(51) Int. Cl.
*G16H 30/40* (2018.01)
*A61B 6/00* (2006.01)
*A61N 7/00* (2006.01)

(52) U.S. Cl.
CPC ........... *G16H 30/40* (2018.01); *A61B 6/5205* (2013.01); *A61N 7/00* (2013.01)

(58) Field of Classification Search
CPC ........ G16H 30/40; A61B 6/5205; A61N 7/00; A61N 7/02; G06T 11/006; G06T 11/008
See application file for complete search history.

(56) References Cited

U.S. PATENT DOCUMENTS

| | | | | |
|---|---|---|---|---|
| 10,699,163 | B1* | 6/2020 | Shah | G06F 18/214 |
| 2005/0220711 | A1* | 10/2005 | Katz | A61N 7/00 424/9.5 |
| 2013/0094729 | A1* | 4/2013 | Mauldin, Jr. | A61B 8/5207 382/128 |
| 2017/0055931 | A1 | 3/2017 | Paysan et al. | |
| 2017/0340287 | A1 | 11/2017 | Fulton et al. | |
| 2019/0298304 | A1* | 10/2019 | Igarashi | A61B 8/5207 |
| 2020/0164231 | A1 | 5/2020 | Cannata et al. | |
| 2021/0093897 | A1 | 4/2021 | Zadicario et al. | |

FOREIGN PATENT DOCUMENTS

WO WO 2019069135 A1 4/2019

* cited by examiner

*Primary Examiner* — Bo Joseph Peng
(74) *Attorney, Agent, or Firm* — Harness, Dickey & Pierce, P.L.C.

(57) ABSTRACT

In a computer-implemented method, a three-dimensional medical image of an examination object is created taking into consideration at least one temporally and/or spatially variable cavitation bubble in the examination object. The cavitation bubble is created by at least one ultrasound pulse emitted by an ultrasound system into the examination object. The computer-implemented method comprises: acquiring a multiplicity of projection images of the examination object with a medical imaging system; determining at least one cavitation bubble projection image from the multiplicity of projection images as a function of a synchronization between a medical imaging system and the ultrasound system; determining a multiplicity of corrected projection images; reconstructing the three-dimensional medical image as a function of the multiplicity of corrected projection images; and provisioning the three-dimensional medical image.

20 Claims, 6 Drawing Sheets

METHOD FOR CREATING A THREE-DIMENSIONAL MEDICAL IMAGE

CROSS-REFERENCE TO RELATED APPLICATION(S)

The present application claims priority under 35 U.S.C. § 119 to German Patent Application No. 10 2021 212 141.1, filed Oct. 27, 2021, the entire contents of which are incorporated herein by reference.

BACKGROUND

It is known that an intervention or treatment of an examination object, in particular of a patient, can be monitored with medical imaging. A three-dimensional medical image can be created for monitoring via medical imaging. To create the three-dimensional medical image a multiplicity of two-dimensional projection images of the examination object is typically acquired with a medical imaging system. Then the three-dimensional medical image can be reconstructed as a function of these projection images. The multiplicity of projection images in this case maps the examination object from different angles. In this case each projection image maps the examination object from another angle.

The medical imaging system can in particular be a computed tomography system or a C-arm system. The multiplicity of projection images is then a multiplicity of two-dimensional x-ray images that image the examination object from different angles or mapping angles.

The multiplicity of projection images is typically acquired as a temporal sequence. In other words the projection images are typically acquired one after another over time or sequentially with the medical imaging system. When the examination object or a part of the examination object changes between the individual projection images this can lead to an image error in the three-dimensional medical image. In other words a change in the examination object between the individual projection images leads to an inconsistency in the reconstruction and thus to an image error in the three-dimensional medical image.

This type of temporal change in the examination object can for example be caused by radiating or introducing a focused high-energy ultrasound pulse into the examination object. The ultrasound pulse can be radiated or introduced into the examination object with an ultrasound probe or an ultrasound transducer. In this case the focus of the ultrasound pulse lies within the examination object. In the focus of the ultrasound pulse or in the environment of the focus of the ultrasound pulse at least one vapor-filled bubble, known as a cavitation bubble, is created in the examination object. This cavitation bubble arises as a result of the input of energy by the ultrasound pulse as a result of temperature changes and/or pressure changes. The cavitation bubble can change over time and/or in space. In other words the cavitation bubble is temporally and/or spatially variable. The ultrasound pulse can be radiated into the examination object for a histotripsy treatment for example.

SUMMARY

An image error in a three-dimensional medical image, which arises from the inconsistencies in the projection images, can lead to the monitoring of the intervention only being possible to a limited extent. For example the image error can overlay a bleeding in the three-dimensional medical image.

An object of one or more example embodiments of the present invention is therefore to provide a method with which an image error in a three-dimensional medical image of an examination object, which arises from a temporal variation of the examination object, can be corrected.

At least this object is achieved by a method for creating a three-dimensional medical image of an examination object, while taking into consideration at least one temporally and/or spatially variable cavitation bubble in the examination object, by a system for creating a three-dimensional medical image of an examination object, while taking into consideration at least one temporally and/or spatially variable cavitation bubble in the examination object, by a computer program product and by a computer-readable memory medium, according to one or more example embodiments of the present invention, and as claimed in the independent claims. Advantageous developments are given the dependent claims and in the following description.

An inventive way in which the object is achieved is described below both with regard to the claimed apparatuses and also with regard to the claimed method. Features, advantages or alternative forms of embodiment mentioned here are likewise also to be transferred to the other claimed subject matter and vice versa. In other words the physical claims (which can be directed to an apparatus for example) can also be further developed with the features that are described or claimed in conjunction with a method. The corresponding functional features of the method are embodied in this case by corresponding physical modules.

One or more example embodiments of the present invention relate to a computer-implemented method for creating a three-dimensional image of an examination object, while taking into consideration at least one temporally and/or spatially variable cavitation bubble in the examination object. In this case the at least one cavitation bubble is caused by at least one ultrasound emitted into the examination object by an ultrasound system. The method comprises a method step of acquiring a multiplicity of projection images of the examination object with a medical imaging system. In this case the medical imaging system is synchronized with the ultrasound system. The method moreover comprises a method step of determination of at least one cavitation bubble projection image from the multiplicity of projection images as a function of the synchronization. In this case the at least one cavitation bubble projection image is one projection image of the multiplicity of projection images in which the at least one cavitation bubble is mapped. The method moreover comprises a method step of determination of a multiplicity of corrected projection images. In this case, in the multiplicity of corrected projection images, the at least one cavitation bubble projection image of the multiplicity of projection images is replaced by a corresponding corrected projection image. The method moreover comprises a method step of a reconstruction of the three-dimensional medical image as a function of the multiplicity of corrected projection images. The method moreover comprises a method step of provision of the three-dimensional medical image.

The examination object can be a human being, an animal or an object. The examination object can be a part of a human being, an animal or an object. The examination object comprises a material that forms at least one cavitation bubble in the focus of the ultrasound pulse. The cavitation bubble can be filled with a gas or vapor and/or a fluid. In particular a multiplicity of cavitation bubbles can have been formed or created in the focus of the ultrasound pulse in the examination object.

The at least one cavitation bubble is spatially and/or temporally variable. Temporally variable in this case means that the cavitation bubble varies its shape and/or its size over the course of time. In particular temporally variable can mean that the cavitation bubble only exists in a specific time interval. Before and after this time interval the cavitation bubble does not exist in the examination object. Spatially variable means that the cavitation bubble changes or varies its location within the examination object over time. In other words spatially variable means that the cavitation bubble diffuses through the examination object. In other words spatially variable means that the at least one cavitation bubble moves in the examination object.

The ultrasound pulse is a high-intensity focused ultrasound pulse. The ultrasound pulse is radiated into the examination object with the ultrasound system. For this the ultrasound system comprises an ultrasound probe. The ultrasound probe emits the focused high-intensity ultrasound pulse. To introduce the ultrasound pulse into the examination object the ultrasound probe is brought into contact with the examination object. In particular a coupling medium can be introduced between the ultrasound probe and the examination object in order to optimize the coupling of the ultrasound pulse into the examination object. The coupling medium can be a contact gel or an ultrasound gel.

In the method step of acquisition of a multiplicity of projection images, the multiplicity of projection images of the examination object is acquired with the medical imaging system. The medical imaging system can be a computed tomography system or a C-arm system. The projection images are thus in particular x-ray images. To acquire a projection image the examination object is arranged between an x-ray tube and an x-ray detector, when the medical imaging system is a computed tomography system or a C-arm system. In this case the medical imaging system comprises the x-ray tube and the x-ray detector. X-rays emitted by the x-ray tube, after passing through the examination object, are detected by the x-ray detector. In this way the x-ray detector acquires the projection images.

The projection images are two-dimensional. Each projection image comprises a multiplicity of pixels, which are arranged in a two-dimensional pixel matrix. Each pixel is assigned a pixel value. The pixel value in this case describes an intensity value which maps the examination object of the position of the pixel. In other words the pixel value describes the projection of the examination object onto the pixel. The projection depends in this case on material properties of the examination object.

The projection images map the examination object. Each projection image is acquired at a different angle to the examination object. In other words the x-ray tube and in many embodiments also the x-ray detector carry out a pivoting movement about the examination object during acquisition of the projection images. In this case each projection image is acquired at a different angle or mapping angle relative to the examination object. In this case the projection images can be acquired in an angular range of 90°, 100°, 110°, 120°, 130°, 140°, 150°, 160°, 170°, 180°, 200°, 210°, 270° or 360°. In other words the pivot during acquisition of the projection images can cover one of the said angular ranges. Moreover the projection images are acquired in a time sequence, i.e. at different points in time.

The medical imaging system and the ultrasound system are synchronized with one another. In other words the acquisition of the projection images and the emission of the ultrasound pulse is synchronized. Synchronized means that the medical imaging system and the ultrasound system are at least synchronized in time. Synchronized in time means that a temporal relationship between the emission of the ultrasound pulse and the acquisition of the individual projection images is known. For example it is known whether a projection image was acquired before or after the emission of the ultrasound pulse. In particular it can moreover be known how long before the emission of the ultrasound pulse the projection image was acquired. In versions of embodiments of the present invention, "synchronized" can additionally mean that the medical imaging system and the ultrasound system are spatially synchronized. Spatially synchronized can mean that a spatial relationship of a location of the focus of the ultrasound pulse in the examination object and of the mapping of the corresponding location in the projection images is known.

In the method step of determination of the at least one cavitation bubble projection image the at least one cavitation bubble projection image is determined from the multiplicity of the projection images. In other words at least one of the projection images is classified as a cavitation bubble projection image. The at least one cavitation bubble projection image maps the at least one cavitation bubble in the examination object. In particular each of the projection images that maps the at least one cavitation bubble is a cavitation bubble projection image. The at least one cavitation bubble projection image is determined as a function of the synchronization of the medical imaging system and the ultrasound system.

With a temporal synchronization in particular a projection image that was acquired after the beginning of the emission of the ultrasound pulse can be determined or classified as a cavitation bubble projection image. In particular all projection images that were acquired after the beginning of the emission of the ultrasound pulse can be determined or classified as cavitation bubble projection images.

When the emission of the ultrasound pulse or the point in time of the emission of the ultrasound pulse are discussed below, it is always the beginning of the emission of the ultrasound pulse that is meant.

In versions of embodiments of the present invention, it can be known for how long a cavitation bubble exists in an examination object. A duration of the existence of the cavitation bubble in the examination object can be known from experience. As an alternative or in addition the duration of the existence can be determined via a simulation or by modeling. In other words a time interval can be determined in which the at least one cavitation bubble exists. A projection image that has been acquired with a greater temporal spacing from the point in time of the emission of the ultrasound pulse than the duration of the existence of the cavitation bubble is not then determined as a cavitation bubble projection image. In particular all projection images that were acquired after the emission of the ultrasound pulse within the time interval determined can be determined or classified as cavitation bubble projection images.

In the method step of determination of the multiplicity of corrected projection images, the multiplicity of corrected projection images is determined as a function of the multiplicity of projection images and the at least one cavitation bubble projection image. The multiplicity of corrected projection images in this case comprises the projection images of the multiplicity of projection images that do not map the at least one cavitation bubble or that have not been classified as cavitation bubble projection images. The at least one cavitation projection image is replaced in the multiplicity of the corrected projection images by the corresponding corrected projection image. In other words the multiplicity of corrected projection images, instead of the at least one cavitation bubble projection image, comprises the at least one corresponding corrected projection image.

In the corrected projection image in particular the region of the corresponding cavitation bubble projection images that maps the at least one cavitation bubble is corrected. In other words, in the corrected projection image, the region in the cavitation bubble projection image that maps the at least one cavitation bubble is processed in such a way that an inconsistency caused by the at least one variable cavitation bubble in the multiplicity of projection images is reduced or removed and the image error in the three-dimensional medical image is minimized.

In the method step of reconstruction of the three-dimensional medical image the three-dimensional medical image is reconstructed as a function of the multiplicity of corrected projection images. In this case the three-dimensional medical image can be reconstructed with a standard algorithm or a known algorithm for reconstruction of a three-dimensional medical image from a multiplicity of projection images. The standard algorithm can for example comprise a form of filtered back projection. The three-dimensional medical image maps the examination object three-dimensionally. The three-dimensional medical image comprises a multiplicity of voxels, which are arranged in a voxel matrix. Each voxel comprises a voxel value. The voxel value describes a property, in particular a material property, of the examination object at the corresponding point of the examination object.

In the method step of provision of the three-dimensional medical image the medical image is provided to a person, for example a physician or a medical assistant. The three-dimensional medical image in this case can be displayed to the person on a display unit. The display unit can in particular be a monitor or screen and/or a tablet. As an alternative or in addition, in the method step of provision of the three-dimensional medical image, the three-dimensional medical image can be stored. In particular the three-dimensional medical image can be stored in a database on a server. The database can for example be a Picture Archive and Communication System (acronym: PACS). The server in this case can be a local server or a cloud server.

The inventor has recognized that via the synchronization the at least one projection image can be determined that maps the at least one cavitation bubble. This at least one cavitation bubble projection image can lead to an image error in the three-dimensional medical image. The inventor has recognized that, by correcting this at least one cavitation bubble projection image before the reconstruction of the three-dimensional medical image, the image error in the three-dimensional medical image can be prevented or reduced.

According to one aspect of an embodiment the present invention, the method step of determination of the multiplicity of corrected projection images comprises a method step of reconstruction of a provisional three-dimensional medical image with a standard algorithm as a function of the multiplicity of projection images. The method step of determination of the multiplicity of corrected projection images moreover comprises a method step of determination of a multiplicity of provisional projection images by forward projection of the provisional three-dimensional medical image. In this case each of the provisional projection images corresponds to precisely one projection image. The method step of determination of the multiplicity of corrected projection images moreover comprises a method step of determination of a multiplicity of difference projection images by subtraction of one or more projection images from the respective corresponding provisional projection image. The method step of determination of the multiplicity of corrected projection images moreover comprises a method step of filtering the multiplicity of difference projection images. In this case at least those difference projection images that do not map the at least one cavitation bubble are weighted. The method step of determination of the multiplicity of corrected projection images moreover comprises a method step of adding one or more projection images with the respective corresponding filtered difference projection image. Through this the multiplicity of corrected projection images is determined.

In the method step of reconstruction of the provisional three-dimensional medical image the provisional three-dimensional medical image is reconstructed as a function of the projection images. For this a standard algorithm as described above is applied to the multiplicity of projection images. The provisional three-dimensional medical image can in particular comprise or map the image error as a result of the inconsistencies in the projection images on account of the at least one cavitation bubble.

In the method step of determination of a multiplicity of provisional projection images, a provisional projection image is determined for each projection image of the multiplicity of projection images by forward projection of the provisional three-dimensional medical image. A provisional projection image maps the examination object from the same angle as the projection image corresponding to the provisional projection image.

In the method step of determination of the multiplicity of difference projection images the multiplicity of difference projection images is determined by subtraction of one or more projection images from the respective corresponding provisional projection image. In particular, for determination of the difference projection images, each of the projection images can be subtracted from the respective corresponding provisional projection image. In other words, for at least one, in particular for each pair, of a projection image and a provisional projection image, a difference projection image is determined. For this the projection image is subtracted from the corresponding provisional projection image. In this case the projection image and the provisional projection image are subtracted from one another pixel-by-pixel. In particular a difference projection image is thereby assigned to a respective projection image and a provisional projection image. In other words each difference projection image corresponds to a projection image and a provisional projection image.

In the method step of filtering of the multiplicity of difference projection images at least the difference projection images that do not map the at least one cavitation bubble are weighted. In other words those difference projection images are weighted that are not assigned to a cavitation bubble projection image. In particular the weights of the said difference projection images enable the said difference projection images to be weighted lower than the at least one difference projection image that corresponds to the at least one cavitation bubble projection image.

In the method step of addition, one or more projection images of the multiplicity of projection images is added to the filtered difference projection image corresponding to the respective projection image corresponding. In particular each projection image is added to the difference projection image corresponding to the projection image. In particular a projection image and the corresponding filtered difference projection image are added pixel-by-pixel. In other words the pixel values of two pixels corresponding to one another are added.

In this case the multiplicity of the corrected projection images comprises the results of this addition.

The inventor has recognized that the image error in the provisional three-dimensional medical image, i.e. in the image that is reconstructed as a function of the originally acquired multiplicity of projection images, can be used in order to determine the multiplicity of corrected projection images. The inventor has recognized that, through the forward projection, the provisional three-dimensional medical image of the image error can be transferred into the "domain" of the projection image. From this it can be deduced where the at least one cavitation bubble was in the examination object during the acquisition of the projection images. On the basis of this the projection images that map the at least one cavitation bubble can be corrected.

According to a further aspect of an embodiment of the present invention, the method steps of reconstruction of the provisional three-dimensional medical image, of determination of the multiplicity of provisional projection images, of determination of the multiplicity of difference projection images, of filtering of the multiplicity of difference projection images and of addition of each projection image to the corresponding filtered difference projection image can be repeated iteratively until an abort criterion is fulfilled. In this case, in the second and further iterations, the provisional three-dimensional image is determined as a function of the multiplicity of corrected projection images determined in the previous iteration.

The said method steps are carried out in a first iteration as described above. In a second iteration the said method steps are repeated, with the difference that the provisional three-dimensional medical image is determined as a function of the multiplicity of corrected projection images determined in the first iteration. All other said method steps are carried out similarly to the first iteration. In a third iteration the method steps are again carried out in a similar way with the difference that the provisional three-dimensional medical image of the third iteration is determined as a function of the multiplicity of corrected projection images of the second iteration. In this way any given number of iterations can be carried out until the abort criterion is fulfilled. On fulfillment of the abort criterion the multiplicity of corrected projection images corresponds to the last iteration of the final multiplicity of corrected projection images. Then, as a function of this final multiplicity of corrected projection images, the three-dimensional medical image can be reconstructed in the method step of reconstruction of the three-dimensional medical image.

The inventor has recognized that the correction of the projection images, in particular of the cavitation bubble projection images, can be optimized when the previously described method steps are carried out iteratively to determine the multiplicity of corrected projection images.

According to a further aspect of an embodiment of the present invention, the abort criterion is at least one of the following criteria: a maximum number of iterations, a maximum deviation between the provisional projection images of two consecutive iterations or a maximum deviation between the provisional three-dimensional medical images of two consecutive iterations.

The maximum number of iterations specifies how many iterations as a maximum are to be carried out for determination of the multiplicity of corrected medical images. The criterion is thus fulfilled when the number of iterations carried out corresponds to the maximum number.

In order to determine the deviation between the provisional projection images of two consecutive iterations, a provisional projection image of the one iteration is subtracted pixel-by-pixel from the corresponding provisional projection image of the next iteration in each case. In this case the pixel values of two pixels of the provisional projection images corresponding to one another are subtracted from one another. Two pixels corresponding to one another are arranged at the same point in the pixel matrix. Two provisional projection images corresponding to one another are the provisional projection images of two iterations that map the examination object from the same angle. Then, from the differences of the pixel values, the root mean square can be determined for example. The root mean square can be determined in a similar way for all pairs of provisional projection images of two consecutive iterations. Then, from the root mean squares determined in this way, a quadratic overall mean can be determined. The quadratic overall mean then describes the deviation between two provisional projection images of two consecutive iterations. The deviation can of course be determined with any given alternative measure of distance.

The maximum deviation between the provisional projection images specifies a value. When the deviation between the provisional projection images of two consecutive iterations falls below this value, no further iteration is carried out. The criterion is thus fulfilled when the deviation between the provisional projection images of two consecutive iterations falls below the maximum deviation. The last multiplicity of corrected projection images determined is then the final multiplicity of corrected projection images.

The deviation between two provisional three-dimensional medical images of two consecutive iterations can be calculated by the provisional three-dimensional medical images being subtracted from one another. In this case the voxel values of two voxels corresponding to one another are subtracted. Two voxels corresponding to one another are arranged at the same position in the voxel matrix of the two provisional three-dimensional medical images. A root mean square can then be determined from the differences of the voxel values, which corresponds to the deviation of the two provisional three-dimensional medical images. Of course the deviation can also be determined with alternatively known measures of distance.

The maximum deviation between the provisional three-dimensional medical images specifies a value. When the deviation between the provisional three-dimensional medical images of two iterations following one another falls below this value, no further iteration is carried out. The criterion is thus fulfilled when the deviation between the provisional three-dimensional medical images of two consecutive iterations falls below the maximum deviation. The last multiplicity of corrected projection images determined is then the final multiplicity of corrected projection images.

The abort criterion can be precisely one of the said criteria. In particular the abort criterion variable can be one of the said criteria, depending on which is fulfilled first. In other words the abort criterion can be any given criterion of the said criteria, so that the fulfillment of a given criterion leads to the iterative carrying out of the method steps being aborted. In this version, when one of the criteria is fulfilled, no further iteration is carried out. As an alternative the abort criterion can be a specific criterion of the said criteria determined beforehand, which must be fulfilled for an abort.

As an alternative the abort criterion can comprise two or all three criteria. In particular the iterative carrying out of the method steps is then only aborted if both or all three criteria are fulfilled.

The inventor has recognized that the three-dimensional medical image is sufficiently well corrected when at least one of the aforementioned abort criteria is fulfilled. In other words the image error in the three-dimensional medical image created by the at least one cavitation bubble can be sufficiently reduced when at least one of the aforementioned criteria is fulfilled as abort criterion.

According to a further aspect of an embodiment of the present invention, in the method step of filtering of the multiplicity of difference projection images, at least those difference projection images that do not map the at least one cavitation bubble are multiplied by a weighting factor. In this case the weighting factor is greater than or equal to zero. In this case the weighting factor is less than 1.

In the method step of filtering of the multiplicity of difference projection images at least one part of the multiplicity of difference projection images can thus be filtered with a weighting factor. In this case the difference projection images that do not map the at least one cavitation bubble can be multiplied by the weighting factor. In other words the projection images that are not a cavitation bubble projection image are multiplied by the weighting factor. In particular the pixel values of the corresponding projection images are multiplied by the weighting factor. The weighting factor can in particular be zero. As an alternative the weighting factor can be less than one. As an alternative "multiply by the weighting factor" can mean that all negative values of the corresponding difference projection images are set to zero and all others are kept unchanged. The multiplicity of the filtered difference projection images comprises the multiplicity of the difference projection images weighted in this way. The multiplicity of the filtered difference projection images also comprises the difference projection images that correspond to a cavitation bubble projection image and are thus not multiplied by the weighting factor.

The weighting factor can in particular be precisely zero. As an alternative the weighting factor can be any given value between zero and one.

The weighting factor is embodied to be multiplied pixel-by-pixel by the difference projection images.

In versions of embodiments of the present invention, the at least one difference projection image that corresponds to the at least one cavitation bubble projection image can be multiplied by a second weighting factor. In particular the pixel values of the at least one cavitation bubble projection image can be multiplied by the second weighting factor. The second weighting factor can be greater than one in this case. In particular the second weighting factor can be between one and two or between one and five.

The inventor has recognized that a weighting factor with a value of between zero and one (inclusive) is especially well suited for determination of the filtered projection images. The inventor has recognized that it can be varied through the weighting factor how heavily the projection images that do not map the at least one cavitation bubble are to be processed. With a weighting factor of zero the projection images that do not map the at least one cavitation bubble remain unchanged and only the cavitation bubble projection images are corrected.

According to a further aspect of an embodiment of the present invention, the method moreover comprises a method step of determination of a spatial environment in which the at least one cavitation bubble is mapped in the at least one cavitation bubble projection image, as a function of the synchronization. In this case, in the method step of filtering of the multiplicity of difference projection images, the difference projection image which corresponds to the at least one cavitation bubble projection image is moreover weighted outside the environment of the at least one cavitation bubble.

The term "environment" is to be understood as an environment or an image region with spatial regard to the at least one cavitation bubble. In other words the environment is a spatial environment.

To determine the environment of the at least one cavitation bubble in the at least one cavitation bubble projection image the medical imaging system and the ultrasound system are synchronized temporally and spatially. In particular it is thus known how long the at least one cavitation bubble projection image was acquired after the emission of the ultrasound pulse. Moreover it is known how the medical imaging system was aligned or positioned relative to the ultrasound system on emission of the ultrasound pulse. In this way it can be determined where in the at least one cavitation bubble projection image the focus of the ultrasound pulse is arranged. In other words the location of the focus of the ultrasound pulse in the at least one cavitation bubble projection image can be determined in this way.

From the position of the focus of the ultrasound pulse in the examination object the position of the focus of the ultrasound pulse in the at least one cavitation bubble projection image can be deduced through the synchronization. In particular it can be deduced in which at least one pixel of the at least one cavitation bubble projection image the focus is positioned. The environment of the at least one cavitation bubble can comprise a multiplicity of pixels of the at least one cavitation bubble projection image around the pixel with the focus of the ultrasound pulse. In particular the environment can comprise a multiplicity of pixels around the at least one pixel that maps the focus. In particular the pixels of the multiplicity of pixels of the environment in this case at a maximum have a maximum spatial distance to the pixels with the focus. In other words the environment can comprise those pixels that comprise a maximum distance to the focus in the cavitation bubble projection image. The maximum spatial distance can be predetermined manually or automatically.

As an alternative a predicted position or a predicted location of the at least one cavitation bubble in the examination object at the time of the acquisition of the at least one cavitation bubble projection image can be simulated or modeled. For this for example the focus can be assumed as the point of origin of the at least one cavitation bubble. Depending on a material of the examination object, the diffusion of the at least one cavitation bubble in the at least one examination object can be simulated or modeled. Depending on a length of time between the emission of the ultrasound pulse and the acquisition of the at least one cavitation bubble projection image, with the aid of the simulation or of the model it can be determined where the at least one cavitation bubble is predicted to be located at the time of the acquisition of the at least one cavitation bubble projection image. From the predicted location in the examination object, depending on the synchronization, the location of at least one pixel of the at least one cavitation bubble projection image that is predicted to map the at least one cavitation bubble can be deduced. The predicted location of the at least one cavitation bubble can be determined with a degree of simulation model-dependent and/or examination object-dependent uncertainty. This uncertainty can be taken into consideration in determining the environment. In particular the environment can comprise the pixels in the environment of the at least one pixel that is predicted to map the at least one cavitation bubble, in which the at least one cavitation bubble can still be found with a specific probability that is greater than a lower value. This probability can likewise be determined with the simulation or the model for each pixel. In other words the simulation or the model can provide a map, which for each pixel of the cavitation bubble projection image, comprises a probability that the cavitation bubble is arranged in the corresponding pixel. The lower value can be 90% or 80% or 70% or 60% for example. As an alternative the environment can comprise the pixels that, as described above, at a maximum have a maximum spatial distance from the at least one pixel that is predicted to map the cavitation bubble.

In the method step of filtering of the multiplicity of difference projection images the pixel values of the pixels that are not comprised by the environment of the at least one cavitation bubble are weighted as described above. In versions of embodiments of the present invention, the pixel values of the pixels that are not comprised by the environment can be multiplied for this by the weighting factor described above. "Outside the environment" in this case means that the corresponding pixels of the at least one cavitation bubble projection image are not comprised by the environment.

In versions of embodiments of the present invention, the pixel values of the pixels that are comprised by the environment can be multiplied by the second weighting factor.

The inventor has recognized that the determination of the corrected projection images can be optimized still further when additionally the spatial synchronization is used to determine the predicted position of the at least one cavitation bubble in the at least one cavitation bubble projection image. The inventor has recognized that in this way the cavitation bubble projection images can be explicitly corrected in the region influenced by the at least one cavitation bubble. In particular in this way the number of iterations needed to determine the multiplicity of corrected projection images can be reduced.

According to a further aspect of an embodiment of the present invention, the method step of determination of the multiplicity of corrected projection images comprises a method step of determination of a spatial environment, in which the at least one cavitation bubble is mapped in the at least one cavitation bubble projection image, as a function of the synchronization. Moreover the method step of determination of the multiplicity of corrected projection images comprises a method step of interpolation of the environment of the at least one cavitation bubble as a function of neighboring image regions in the at least one cavitation bubble projection image.

In this case the method step of determination of the environment can be embodied as described above. In this case the environment is embodied as described above. In particular the environment describes a spatial relationship with a position or a location of the at least one cavitation bubble in the at least one cavitation bubble projection image.

In the method step of interpolation the pixel values of the pixels of the at least one cavitation bubble projection image that are comprised by the environment are replaced by interpolation values. To determine the interpolation values an interpolation based on the "residual" pixel values of the at least one cavitation bubble projection image is carried out. In particular the interpolation is carried out as a function of the environment the image regions the at least one cavitation bubble projection adjoining or in the neighborhood of the at least one cavitation bubble. In other words the interpolation values depend on the pixel values in the neighboring image regions.

The method step of interpolation can be carried out by a standard method for closing up error points in image data. In particular in this case the error point, i.e. the environment of the at least one cavitation bubble in the at least one cavitation bubble projection image, is closed up by a constant interpolation between the adjoining image regions. As an alternative the method step of interpolation can comprise an application of a trained function to the at least one cavitation bubble projection image. The trained function is embodied in this case meaningfully to replace an image region in an image. The trained function in this case can in particular comprise a convolutional neural network.

The at least one cavitation bubble projection image interpolated in this way is then the corrected projection image that, instead of the cavitation bubble projection image, is comprised by the multiplicity of corrected projection images.

The inventor has recognized that the corrected projection image that is to replace the at least one cavitation bubble projection image can be determined by an interpolation of the environment of the at least one cavitation bubble in the cavitation bubble projection image. In particular in this way the cavitation bubble projection image can be corrected in such a way that it has no inconsistencies or slight inconsistencies as a result of the at least one cavitation bubble with the other projection images. The inventor has recognized that, depending on the projection images that do not map the at least one cavitation bubble and the at least one projection image corrected in this way, the three-dimensional medical image can be reconstructed. In particular in this way the image error in the three-dimensional medical image caused by the at least one cavitation bubble can be prevented or reduced.

According to a further aspect of an embodiment of the present invention, the environment of the at least one cavitation bubble in the at least one cavitation bubble projection image is determined as a function of point in time of the emission of the ultrasound pulse and/or as a function of a trajectory of a focus of the ultrasound pulse in the examination object and/or based on an ultrasound imaging, which represents the at least one cavitation bubble in the examination object.

The synchronization enables it to be deduced from the point in time of the emission of the ultrasound pulse which of the projection images is the at least one cavitation bubble projection image that comprises the environment of the at least one cavitation bubble. As described above, the point in time of the emission of the ultrasound pulse relates in this case to the point in time of the beginning of the emission of the ultrasound pulse. In particular however the duration of the ultrasound pulse can also be taken into consideration below when cavitation bubbles are created in the examination object over the entire duration. With a simulation or a model embodied as described above, as a function of the time difference or of the time interval or the length of time between the emission of the ultrasound pulse and the acquisition of the at least one cavitation bubble projection image it can be simulated or modeled where the at least one cavitation bubble has diffused to in the examination object at the point in time of the acquisition of the at least one cavitation bubble projection image. In other words the predicted location or the predicted position of the at least one cavitation bubble in the examination object can be simulated or modeled as a function of the point in time of the emission of the ultrasound pulse. In versions of embodiments of the present invention, in this case at least one material of the examination object or a material composition of the examination object can also be taken into consideration. In other words a material property of the examination object can also be taken into consideration. The environment of the at least one cavitation bubble can be related as described above to the predicted location of the cavitation bubble.

In some applications more than one high-intensity focused ultrasound pulse is emitted and radiated into the examination object. In particular the focuses of the different ultrasound pulses can be arranged at different positions or locations in the examination object. In particular the focuses of the different ultrasound pulses can describe a trajectory in the examination object. Through each ultrasound pulse at least one cavitation bubble can be created. In other words each of the ultrasound pulses can create at least one cavitation bubble. In particular the at least one cavitation bubble is created in the focus of an ultrasound pulse. Depending on the trajectory of the focus it can be determined where in the examination object at least one cavitation bubble has been created. Through the temporal synchronization it can moreover be determined at which point in time the different ultrasound pulses have been emitted and what the relationship is between these points in time and the point in time of the acquisition of the at least one cavitation bubble projection image. In particular, as described above, the predicted location or position of the at least one cavitation bubble can be determined from the position of the focus, the point in time of the emission and in some embodiments the material or the material composition or the material property of the examination object.

In particular an occurrence and/or a diffusion of the at least one cavitation bubble in the examination object can be acquired with ultrasound imaging. Via the ultrasound imaging an ultrasound image can be acquired. Via the ultrasound imaging the at least one cavitation bubble in the examination object can be shown at different points in time in the ultrasound image. In particular the predicted location of the at least one cavitation bubble in the examination object can be derived or determined from the ultrasound image. In this case the ultrasound imaging can in particular be carried out with the ultrasound system. As an alternative the ultrasound imaging can be carried out with a second ultrasound system. In this case the second ultrasound system is advantageously synchronized temporally and/or spatially with the medical imaging system and/or the ultrasound system. The synchronization enables the at least one pixel that maps the at least one cavitation bubble in the at least one cavitation bubble projection image to be deduced from the predicted location of the at least one cavitation bubble in the examination object determined by the ultrasound image. From this in its turn, as described above, the environment of the at least one cavitation bubble can be determined.

The inventor has recognized that in particular the temporal and/or spatial synchronization is necessary for determining the environment of the at least one cavitation bubble. The inventor has recognized that this also applies for a multiplicity of ultrasound pulses, of which the focuses image a trajectory in the examination object. The inventor has recognized that the diffusion of the at least one cavitation bubble in the examination object can be monitored or observed or represented visually via ultrasound imaging. The inventor has recognized that, as a result of the synchronization, the predicted location of the at least one cavitation bubble at the point in time of the acquisition of the at least one cavitation bubble projection image can be deduced or this can be determined from the ultrasound image.

According to a further aspect of an embodiment of the present invention, the method step of determination of the multiplicity of corrected projection images comprises a method step of providing an earlier three-dimensional medical image of the examination object. The method step of determination of the multiplicity of corrected projection images moreover comprises a method step of reconstruction of a provisional three-dimensional medical image with a standard algorithm as a function of the multiplicity of projection images. The method step of determination of the multiplicity of corrected projection images moreover comprises a method step of determination of a spatial environment of the at least one cavitation bubble in the provisional three-dimensional medical image and in the at least one cavitation bubble projection image as a function of the synchronization. The method step of determination of the multiplicity of corrected projection images moreover comprises a method step of registering the provisional three-dimensional medical image with the earlier three-dimensional medical image. The method step of determination of the multiplicity of corrected projection images moreover comprises a method step of replacing the environment of the at least one cavitation bubble in the provisional three-dimensional medical image by the corresponding environment in the earlier three-dimensional medical image. The method step of determination of the multiplicity of corrected projection images moreover comprises a method step of determination of a multiplicity of provisional projection images by forward projection of the provisional three-dimensional medical image. In this case each of the provisional projection images is assigned precisely one projection image. The method step of determination of the multiplicity of corrected projection images moreover comprises a method step of replacing the environment of the at least one cavitation bubble in the at least one cavitation bubble projection image by the corresponding region from the corresponding provisional projection image.

In the method step of provision of the earlier three-dimensional medical image an earlier three-dimensional medical image of the examination object is provided. In this case the earlier three-dimensional medical image can be loaded from a database or provided by the database. The database can in particular be a Picture Archiving and Communication System (acronym: PACS). As an alternative the earlier three-dimensional medical image can be provided manually via a memory medium.

The earlier three-dimensional medical image was reconstructed as a function of a multiplicity of earlier projection images. The earlier projection images were advantageously acquired with the same medical imaging system and the same recording parameters as the projection images. Advantageously none of the earlier projection images maps a cavitation bubble. In versions of embodiments of the present invention, the earlier projection images can have been acquired with a different medical imaging system and/or different recording parameters. Then the earlier three-dimensional medical image can be processed in such a way via image processing methods that it corresponds to the provisional three-dimensional medical image in particular in respect of the range of values of the voxel values.

In the method step of reconstruction of the provisional three-dimensional medical image the provisional three-dimensional medical image is reconstructed as a function of the multiplicity of projection images as described above with a standard algorithm. In this case the provisional three-dimensional medical image can comprise the image error as a result of the at least one cavitation bubble mapped in the at least one cavitation bubble projection image.

In the method step of determination of the spatial environment of the at least one cavitation bubble in the provisional three-dimensional medical image and in the at least one cavitation bubble projection image, the environment is determined as a function of the synchronization.

In this case the environment is identified or defined by its spatial relationship to the at least one cavitation bubble in the corresponding image described above, i.e. in the at least one cavitation bubble projection image or in the three-dimensional medical image. In particular the environment designates image regions that lie in the vicinity of the mapping of the at least one cavitation bubble in the cavitation bubble projection image or the three-dimensional medical image.

In this case the spatial environment in the at least one cavitation bubble projection image can be determined as described above.

The spatial environment of the at least one cavitation bubble in the at least one provisional three-dimensional medical image can be determined in a similar way. For this it can in particular be derived as a function of the synchronization which at least one voxel of the provisional three-dimensional medical image maps the at least one cavitation bubble. In this case all voxels that correspond to a region of the examination object through which the at least one cavitation bubble is diffused during the acquisition of the projection images map the at least one cavitation bubble. The environment can then additionally comprise voxels that describe the uncertainty with which the region of the examination object through which the at least one cavitation bubble is diffused can be specified. The greater the uncertainty, the more voxels the environment of the at least one cavitation bubble comprises. As an alternative or in addition the environment can comprise voxels that have a shorter spatial distance to the voxels that map the at least one cavitation bubble than a maximum spatial distance.

In the method step of registration, the provisional three-dimensional medical image is registered with the earlier three-dimensional medical image. For this the two images are mapped to one another via an in particular affine transformation. In this case a one-to-one correspondence of voxels of the two images can be determined. One voxel in each case from each of the images that map the same region of the examination object, corresponds to one another, are thus registered with one another. Voxels corresponding to one another can also be referred to as corresponding voxels.

In the method step of replacement of the environment in the provisional three-dimensional medical image the voxel values of the voxels comprised by the environment in the provisional three-dimensional medical image are replaced by the voxel values of the voxels of the earlier three-dimensional medical image, which are registered with the voxels comprised by the environment.

In the method step of determination of the multiplicity of provisional projection images the multiplicity of the provisional projection images is determined by forward projection of the provisional three-dimensional medical image processed in this way. In this case the provisional projection images are determined in such a way that each provisional projection image is assigned a projection image. Two projection images assigned to one another map the examination object from the same angle. The provisional projection images are thus determined by forward projection of the provisional three-dimensional medical image, in which the environment of the at least one cavitation bubble was replaced as described above.

In the method step of replacement of the environment of the at least one cavitation bubble in the at least one cavitation bubble projection image, the environment is replaced by the corresponding region from the assigned provisional projection image. In other words the pixel values of the pixels comprised by the environment of the at least one cavitation bubble projection image are replaced by the pixel values of the corresponding pixels of the provisional projection image assigned to the cavitation bubble projection image. In this case the two projection images assigned to one another comprise the same number of pixels, which are arranged identically in a pixel matrix in each case. Pixels that are arranged in each case at the same position in the pixel matrix are referred to as corresponding pixels.

The cavitation bubble projection image in which the environment of the at least one cavitation bubble was replaced in such a way is the corresponding corrected projection image.

The multiplicity of corrected projection images, as well as the projection images that do not map the at least one cavitation bubble, then comprises the corrected projection image.

The inventor has recognized that the image region in the provisional three-dimensional medical image and in the at least one cavitation bubble projection image influenced by the at least one cavitation bubble can be corrected based on an earlier three-dimensional medical image. The inventor has recognized that a replacement of the corresponding image regions, in particular of the environment of the at least one cavitation bubble in the provisional three-dimensional medical image and, based thereon, in the at least one cavitation bubble projection image, can correct or avoid or reduce the image error in the three-dimensional medical image.

According to a further aspect of an embodiment of the present invention, the ultrasound system and the medical imaging system are synchronized temporally and/or spatially with one another.

The synchronization is embodied in this case as described above.

The inventor has recognized that it is possible through the temporal synchronization to determine in which of the projection images the at least one cavitation bubble is mapped. The inventor has moreover recognized that it is possible through the temporal and the spatial synchronization to determine where in the at least one cavitation bubble projection image the at least one cavitation bubble is mapped.

According to a further optional aspect of an embodiment of the present invention, in the method step of acquisition of the multiplicity of projection images, the individual projection images are acquired based on the temporal synchronization depending on a point in time of an emission of the ultrasound pulse.

Based on the temporal synchronization the individual projection images can for example be acquired precisely when the ultrasound pulse is not being emitted. As an alternative the individual projection images can be acquired when a sufficiently long period of time has passed after the emission of the ultrasound pulse, so that it can be assumed that a cavitation bubble no longer exists in the examination object. As an alternative the individual projection images can be acquired when, depending on the time of the emission of the ultrasound pulse, it can be assumed that especially many cavitation bubbles exist in the examination object at the time that the projection images are acquired. The desired point in time for acquisition of the projection images can be determined depending on the temporal synchronization and a modeling or simulation of the at least one cavitation bubble and/or an ultrasound imaging.

In versions of embodiments of the present invention, the ultrasound imaging described above can be synchronized temporally with the emission of the ultrasound pulse and with the medical imaging system during acquisition of the multiplicity of projection images. For example at the time of acquisition of the projection images ultrasound images can be acquired at the same time, in order to assess a situation relating to the cavitation bubbles in the examination object based on the ultrasound imaging at the time of the acquisition of the projection images. As an alternative or in addition an ultrasound image can be acquired just when no projection image is being acquired, in order to check the situation with regard to cavitation bubbles in the examination object and where necessary to determine a suitable time to acquire the individual projection images.

The situation relating to the cavitation bubbles in the examination object in particular describes an existence of at least one cavitation bubble in the examination object and, when at least one cavitation bubble exists, a location or position of the at least one cavitation bubble in the examination object.

The inventor has recognized that, based on the temporal synchronization of the ultrasound system and of the medical imaging system, the individual projection images can be acquired at times at which a desired situation exists relating to the cavitation bubbles in the examination object. For example no or as many cavitation bubbles as possible can exist in the examination object at the time of the acquisition of the individual projection images of the multiplicity of projection images in the examination object. The inventor has recognized that optionally also the ultrasound imaging can be synchronized temporally with the emission of the ultrasound pulse and for acquisition of the multiplicity of projection images. The inventor has recognized that in this way the situation regarding the cavitation bubbles can additionally be monitored and where necessary a time for acquiring the multiplicity of projection images can be determined based on at least one ultrasound image.

According to a further aspect of an embodiment of the present invention, the ultrasound system is a histotripsy system. As an alternative or in addition the medical imaging system is an x-ray system.

The histotripsy system is embodied for carrying out a histotripsy treatment or intervention. The histotripsy system comprises an ultrasound therapy transducer, which corresponds to the described ultrasound probe, an ultrasound imaging transducer and a coupling medium. Via the coupling medium, for example a water bath, the ultrasound waves can be radiated or introduced into the material, in particular into the body of the examination object or into the tissue. The ultrasound waves emitted by the ultrasound imaging transducer are used in this case for imaging. In this case at least one ultrasound image can be created. The ultrasound imaging transducer is thus embodied for the ultrasound imaging, with which, as described above, the at least one cavitation bubble in the examination object can be represented. The ultrasound waves emitted by the ultrasound therapy transducer form the high-intensity focused ultrasound pulse and are used for the histotripsy treatment or intervention. In other words the ultrasound therapy transducer forms the ultrasound probe.

The x-ray system comprises an x-ray tube and an x-ray detector. The x-ray system can in particular be a CT system or a C-arm system. The x-ray system is embodied to acquire the multiplicity of projection images.

The inventor has recognized that the method described above can be applied in particular in conjunction with a histotripsy intervention. The inventor has moreover recognized that the projection images in particular can be acquired with an x-ray system.

One or more example embodiments of the present invention moreover relate to a system for creating a three-dimensional medical image of an examination object while taking into consideration at least one temporally and/or spatially variable cavitation bubble in the examination object. In this case the at least one cavitation bubble is caused by at least one ultrasound pulse emitted by an ultrasound system into the examination object. In this case the system comprises an interface and a processing unit. In this case the interface and/or the processing unit is embodied for acquiring a multiplicity of projection images of the examination object with a medical imaging system. In this case the medical imaging system is synchronized with the ultrasound system. In this case the processing unit is moreover embodied to determine at least one cavitation bubble projection image from the multiplicity of projection images depending on the synchronization. In this case the at least one cavitation bubble projection image is a projection image of the multiplicity of projection images in which the at least one cavitation bubble is mapped. In this case the processing unit is moreover embodied to determine a multiplicity of corrected projection images. In this case the at least one cavitation projection image is replaced by a corresponding corrected projection image in the multiplicity of corrected projection images. In this case the processing unit is moreover embodied for reconstruction of the three-dimensional medical image as a function of the multiplicity of corrected projection images. In this case the interface is moreover embodied to provide the three-dimensional medical image.

The system can in particular be embodied to carry out the previously described method for creating a three-dimensional medical image of an examination object while taking into consideration at least one temporally and/or spatially variable cavitation bubble in the examination object and its aspects. The system is embodied to carry out this method and its aspects by the interface and the processing unit being embodied to carry out the corresponding method steps.

One or more example embodiments of the present invention also relate to a computer program product with a computer program as well as to a computer-readable medium. A largely software-based realization has the advantage that even systems already used previously can be upgraded in a simple way by a software update in order to work in the way described. Such a computer program product, as well as the computer program, can where necessary comprise additional elements such as for example documentation and/or additional components, as well as hardware components, such as for example hardware keys (dongles etc.) for using the software.

In particular, one or more example embodiments of the present invention also relate to a computer program product with a computer program, which is able to be loaded directly into a memory of a system, with program sections for carrying out all steps of the method described above for creating a three-dimensional medical image of an examination object while taking into consideration at least one temporally and/or spatially variable cavitation bubble in the examination object and its aspects when the program sections are executed by the system.

In particular, one or more example embodiments of the present invention relate to a computer-readable memory medium, on which program sections able to be read and executed by a system are stored, for carrying out all steps of the method described above for creating a three-dimensional medical image of an examination object while taking into consideration at least one temporally and/or spatially variable cavitation bubble in the examination object and its aspects when the program sections are executed by the system.

BRIEF DESCRIPTION OF THE DRAWINGS

The characteristics, features and advantages of this system described above will become clearer and easier to understand in conjunction with the following figures and their descriptions. In this case the figures and descriptions are not intended to restrict the present invention and its forms of embodiment in any way.

In different figures the same components are provided with corresponding reference numbers. As a rule the figures are not true-to-scale.

In the Figures:

Figure 1:
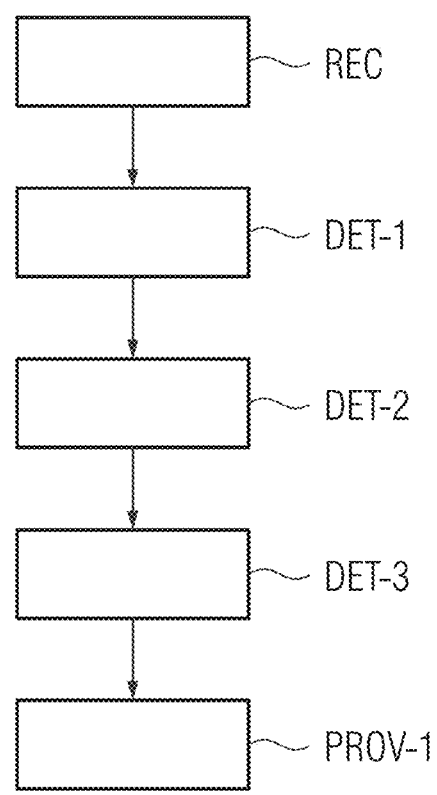
Figure 2:
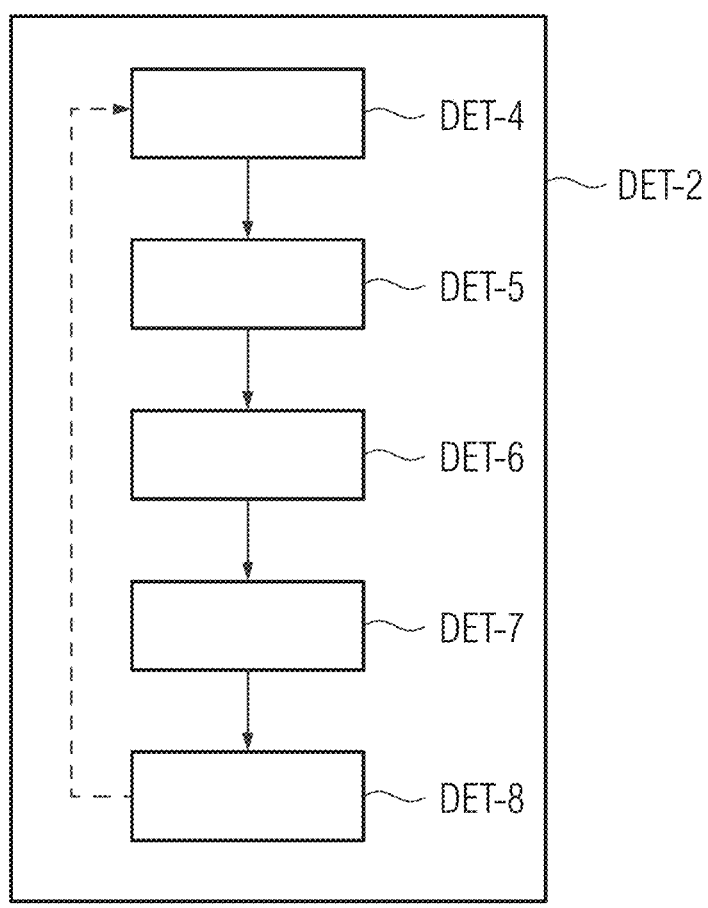
Figure 3:
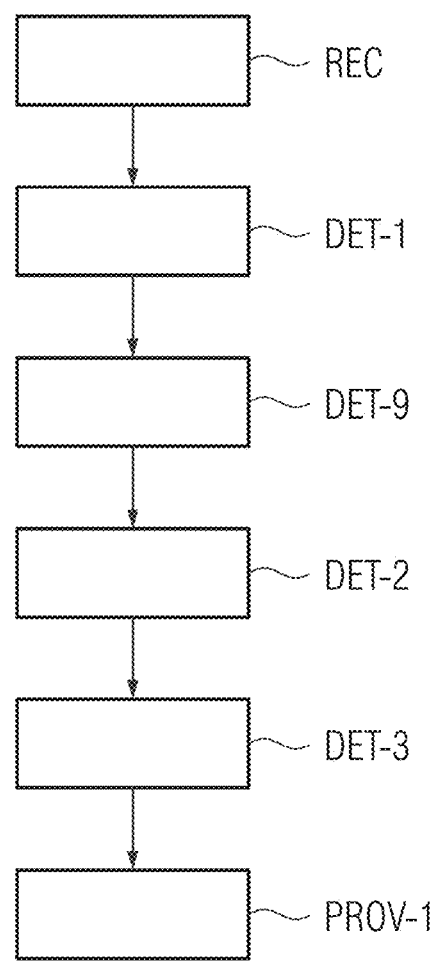
Figure 4:
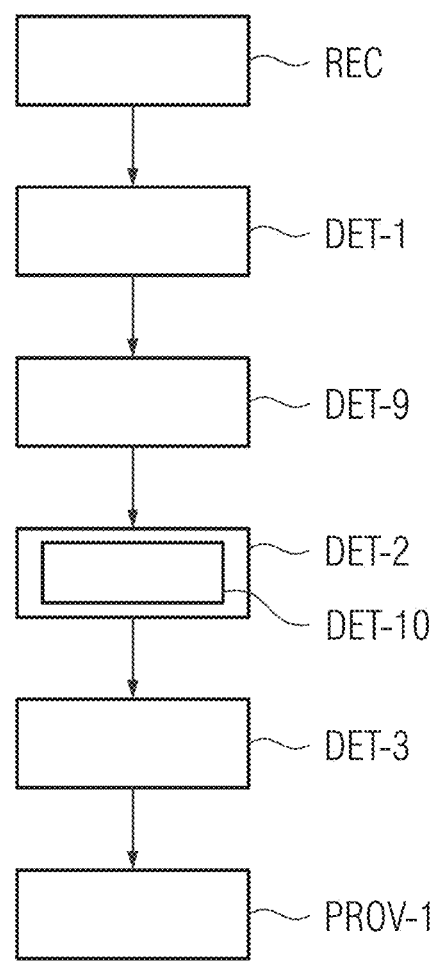
Figure 5:
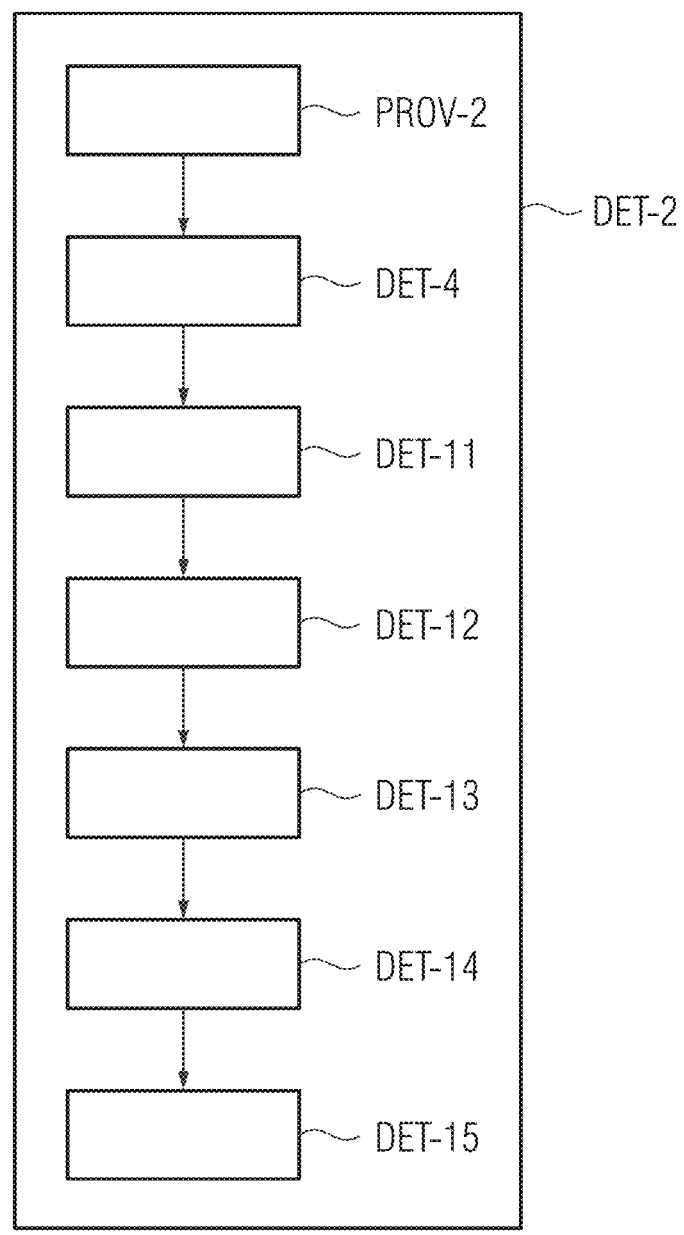
Figure 6:
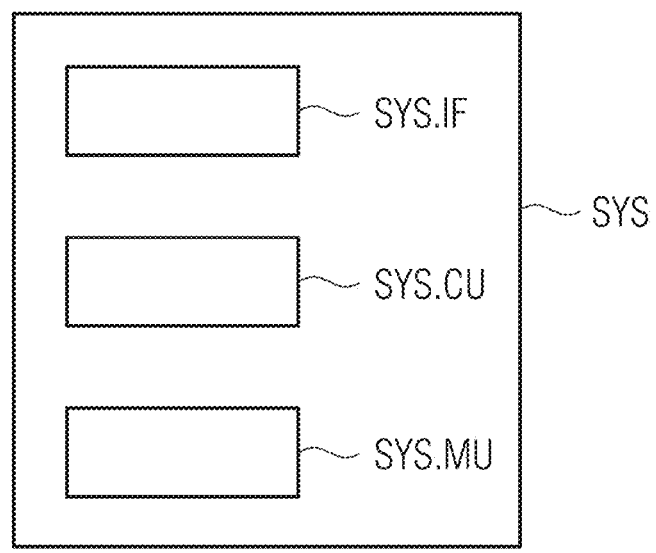

FIG. 1 shows a first exemplary embodiment of a method for creating a three-dimensional medical image of an examination object while taking into consideration at least one temporally and/or spatially variable cavitation bubble in the examination object, FIG. 2 shows a first exemplary embodiment of a method step of determination of a multiplicity of corrected projection images, FIG. 3 shows a second exemplary embodiment of a method for creating a three-dimensional medical image of an examination object while taking into consideration at least one temporally and/or spatially variable cavitation bubble in the examination object, FIG. 4 shows third exemplary embodiment of a method for creating a three-dimensional medical image of an examination object while taking into consideration at least one temporally and/or spatially variable cavitation bubble in the examination object, FIG. 5 shows a second exemplary embodiment of a method step of determination of a multiplicity of corrected projection images, FIG. 6 shows a system for creating a three-dimensional medical image of an examination object while taking into consideration at least one temporally and/or spatially variable cavitation bubble in the examination object.

DETAILED DESCRIPTION

FIG. 1 shows a first exemplary embodiment of a method for creating a three-dimensional medical image of an examination object while taking into consideration at least one temporally and/or spatially variable cavitation bubble in the examination object.

The examination object can be a human being, an animal or an inanimate object. In particular the examination object can be a part of a human being, an animal or an inanimate object. The at least one cavitation bubble is caused or created by an ultrasound pulse, which is radiated or introduced into the examination object. The ultrasound pulse in this case is of high intensity and focused. The ultrasound pulse is caused by an ultrasound system. In particular the ultrasound pulse is emitted by an ultrasound probe, which is comprised by the ultrasound system. For introduction of the ultrasound pulse into the examination object the ultrasound probe is positioned on the examination object or brought into contact with the examination object. In particular the ultrasound probe can be brought into contact with the examination object via a coupling medium, for example a water bath or a contact gel.

In versions of embodiments of the present invention, the ultrasound system can be a histotripsy system. The histotripsy system is embodied to carry out a histotripsy treatment or intervention. The histotripsy system comprises an ultrasound imaging transducer and an ultrasound therapy transducer. The ultrasound therapy transducer corresponds to the ultrasound probe and is embodied to emit the high-intensity, focused ultrasound pulse. Via the ultrasound imaging transducer an ultrasound imaging can be carried out. In other words an ultrasound image can be acquired with the ultrasound imaging transducer. In versions of embodiments of the present invention, for example, the at least one cavitation bubble in the ultrasound image can be displayed via the ultrasound imaging. The histotripsy system thus comprises an ultrasound imaging system and an ultrasound therapy system.

The focus of the ultrasound pulse lies within the examination object. In the focus of the ultrasound pulse or in the immediate vicinity of the ultrasound pulse the ultrasound pulse causes or creates the at least one cavitation bubble. The cavitation bubble can in this case be filled with a gas or vapor or a fluid. The cavitation bubble is spatially and/or temporally variable. Temporally variable means that the cavitation bubble can vary or change its shape over time. Moreover the cavitation bubble can cease to exist or can disappear after a time interval. In particular the cavitation bubble can be absorbed by a material of the examination object. Spatially variable means that the cavitation bubble can diffuse into the examination object. In other words the cavitation bubble moves into the examination object. In other words the location of the at least one cavitation bubble in the examination object is variable.

In a method step of acquiring REC a multiplicity of projection images the multiplicity of projection images of the examination object is acquired with a medical imaging system. The medical imaging system in this case is in particular a computed tomography system or a C-arm system. The projection images are thus two-dimensional x-ray images. The projection images describe projections of the examination object from different angles. The different angles can be produced or brought about by a pivoting of at least one part of the medical imaging system about the examination object during acquisition of the multiplicity of projection images. The projection images are acquired in a time sequence during the pivoting of at least the part of the medical imaging system.

A projection image comprises a multiplicity of pixels, which are arranged in a pixel matrix. Each pixel comprises a pixel value. The pixel value can in particular describe a material property of the part of the examination object that is projected onto the corresponding pixel.

As a result of the spatial and/or temporal variability of the at least one cavitation bubble inconsistencies between the projection images can occur. For example a part of the projection images can have been acquired before the emission of the ultrasound pulse and another part thereafter. As an alternative or in addition the at least one cavitation bubble can move and/or change in its shape between the points in time of the acquisition of different projection images.

Depending on the multiplicity of projection images a provisional three-dimensional medical image can be reconstructed. The variability of the at least one cavitation bubble or the inconsistencies between the projection images give rise to an image error in the provisional three-dimensional medical image. The method makes it possible to correct this image error.

The medical imaging system and the ultrasound system are synchronized. In particular the medical imaging system and the ultrasound system are temporally synchronized. In other words a temporal relationship between the time of the emission of the ultrasound pulse and the times of the acquisition of the projection images is known. In versions of embodiments of the present invention, the medical imaging system and the ultrasound system can additionally be spatially synchronized. In other words it is known how the medical imaging system and the ultrasound system are aligned relative to one another. From this is can be derived for example where in the projection images the focus of the ultrasound pulse is positioned.

In a method step of determination of DET-1 at least one cavitation bubble projection image from the multiplicity of projection images, the at least one cavitation bubble projection image is determined as a function of the synchronization. The at least one cavitation bubble projection image maps the at least one cavitation bubble. In other words the cavitation bubble projection image comprises a mapping of the at least one cavitation bubble. In other words the at least one cavitation bubble projection image is a projection image that maps the at least one cavitation bubble. The determination of the at least one cavitation bubble projection image can comprise a categorization of the projection images according to whether they map the at least one cavitation bubble or not. Those projection images that map the at least one cavitation bubble are categorized or classified as cavitation bubble projection images. In this case more than one projection image can be determined as a cavitation bubble projection image. In other words more than one cavitation bubble projection image can be determined.

The cavitation bubble projection image is in particular determined as a function of the temporal synchronization. In this case it is taken into consideration that the at least one cavitation bubble projection image has been acquired after the emission of the ultrasound pulse. The emission of the ultrasound pulse here designates the point in time of the beginning of the emission of the ultrasound pulse. Moreover the cavitation bubble projection image can have been acquired during a restricted time interval or a restricted period of time after the emission of the ultrasound pulse. After this time interval has elapsed the at least one cavitation bubble can have ceased to exist. A projection image that was thus acquired after this time interval elapsed can no longer map the at least one cavitation bubble. If more than one cavitation bubble was created or has arisen, the time interval is chosen so that, after this time interval has elapsed, all cavitation bubbles have ceased to exist.

In a method step of determination DET-2 of a multiplicity of corrected projection images corrected projection images are determined in which the inconsistencies caused by the at least one cavitation bubble are reduced or removed.

For this, in particular for the at least one cavitation projection image, a corrected projection image can be determined in which the mapping of the at least one cavitation bubble has been removed. The multiplicity of corrected projection images then comprises the multiplicity of projection images, wherein the at least one cavitation projection image has been replaced by the corresponding corrected projection image.

In a method step of reconstruction DET-3 of the three-dimensional medical image the three-dimensional medical image is reconstructed as a function of the multiplicity of corrected projection images. In this case a standard algorithm for reconstruction can be applied to the multiplicity of corrected projection images. The standard algorithm can for example be a filtered back projection or can be based on this.

In a method step of provision PROV-1 of the three-dimensional medical image, the three-dimensional medical image is provided for a further use. In this case the three-dimensional medical image can be stored or held in a database or on a memory medium. The database in this case can be a Picture Archive and Communication System (acronym: PACS). The database can in particular be held on a server. The server can be a local Server or a cloud server.

FIG. 2 shows a first exemplary embodiment of a method step of determination DET-2 of a multiplicity of corrected projection images.

In particular the method step of determination DET-2 of a multiplicity of corrected projection images can be embodied in the method described in the description for FIG. 1 as described below.

The method step of determination DET-2 of a multiplicity of corrected projection images comprises a method step of reconstruction DET-4 of a provisional three-dimensional medical image. The provisional three-dimensional medical image is reconstructed with the standard algorithm described in the description for FIG. 1 as a function of the multiplicity of projection images. The provisional three-dimensional medical image in this case in particular comprises the image error caused by the inconsistencies as a result of the at least one cavitation bubble in the multiplicity of projection images.

The method step of determination DET-2 of the multiplicity of corrected projection images moreover comprises a method step of determination DET-5 of a multiplicity of provisional projection images. The provisional projection images are determined by a forward projection of the provisional three-dimensional medical image. In this case the provisional projection images are determined in such a way that, for each projection image of the multiplicity of projection images a corresponding provisional projection image is determined. Projection images corresponding to one another map the examination object from the same angle. Moreover projection images corresponding to one another advantageously comprise the same number of pixels, which are arranged in pixel matrixes that have the same dimensions.

Through the forward projection the image error from the provisional three-dimensional medical image is transferred to the provisional projection images. As a result of the inconsistencies between the projection images and the image error resulting therefrom the reconstruction is not reversible. For this reason a provisional projection image differs from its corresponding projection image.

The method step of determination DET-2 of the multiplicity of corrected projection images moreover comprises a method step of determination DET-6 of a multiplicity of difference projection images. Each difference projection image corresponds to the difference between a projection image and the corresponding provisional projection image. The difference is determined in this case pixel-by-pixel.

Each difference projection image thus corresponds to a provisional projection image and a projection image or is assigned to these.

The method step of determination DET-2 of the multiplicity of corrected projection images moreover comprises a method step of filtering DET-7 of the multiplicity of difference projection images. In this case those difference projection images of which the corresponding or assigned projection images do not map the least one cavitation bubble are weighted. In particular the difference projection images of which the corresponding projection images do not map the at least one cavitation bubble can be weighted less than the at least one difference projection image that corresponds to the at least one cavitation bubble projection image.

In versions of embodiments of the present invention, the difference projection images of which the corresponding projection images do not map the at least one cavitation bubble, for weighting in the method step of filtering DET-7 of the multiplicity of difference projection images, are multiplied by a weighting factor. In other words those difference projection images are multiplied by the weighting factor that are not assigned to or correspond to the at least one cavitation projection image. The multiplication by the weighting factor is done in this case pixel-by-pixel.

In versions of embodiments of the present invention, the weighting factor can be zero. As an alternative the weighting factor can have a value of between zero and one.

In an optional version of embodiments of the present invention, the at least one cavitation bubble projection image can be multiplied pixel-by-pixel by a second weighting factor. The second weighting factor can in this case be greater than one. In particular the second weighting factor can be a value of between 1 and 2 or between 1 and 5.

The method step of determination DET-2 of the multiplicity of corrected projection images moreover comprises a method step of addition DET-8 of at least one, in particular of each projection image to the corresponding filtered difference projection image. In this case the multiplicity of corrected projection images is determined. In other words the multiplicity of corrected projection images comprises the result images of the addition. The addition is carried out in this case pixel-by-pixel.

In versions of embodiments of the present invention, the method steps of reconstruction DET-4 of the provisional three-dimensional medical image, of determination DET-5 of the multiplicity of provisional projection images, of determination DET-6 of the multiplicity of difference projection images, of filtering DET-7 of the multiplicity of difference projection images and of addition DET-8 of each projection image to the corresponding filtered difference projection image are carried out iteratively. In particular the said method steps are carried out iteratively until such time as an abort criterion is reached.

In the second and all following iterations the provisional three-dimensional medical image is reconstructed in the method step of reconstruction DET-4 of the provisional three-dimensional medical image as a function of the multiplicity of corrected projection images that were determined in the previous iteration. All other said method steps are executed or carried out in a similar way in each iteration.

When the abort criterion is reached or fulfilled no further iteration is carried out. The multiplicity of corrected projection images determined in the last iteration carried out is the (final) multiplicity of corrected projection images, as a function of which, in the method step of reconstruction DET-3 of the three-dimensional medical image, the three-dimensional medical image is reconstructed.

In versions of embodiments of the present invention, the abort criterion can be at least one of the following criteria: a maximum number of iterations, a maximum deviation between the provisional projection images of two consecutive iterations or a maximum deviation between the provisional three-dimensional medical images of two consecutive iterations.

The criterion of the maximum number of iterations specifies how many iterations or how many passes are to be carried out as a maximum. The criterion is fulfilled when the corresponding number of iterations has been carried out.

The criterion of the maximum deviation between the provisional projection images of two consecutive iterations is fulfilled when the deviation between the provisional projection images of two consecutive iterations falls below the value of the maximum deviation. To determine the deviation initially the provisional projection images of two consecutive iterations corresponding to one another are subtracted from one another pixel-by-pixel. Two provisional projection images corresponding to one another map the examination object from the same angle. During subtraction the pixel values of two pixels corresponding to one another are subtracted from one another. Two pixels corresponding to one another are arranged at the same position in the pixel matrixes of the two provisional projection images. Then, for each pair of provisional projection images a root mean square of the differences of the pixel values can be determined. An overall root mean square can be determined as a function of the root mean squares of the pairs of provisional projection images. The deviation is then the overall root mean square of the individual root mean square of the pairs of provisional projection images. Alternative measures of distance for determining the deviation can be used as an alternative.

The criterion of the maximum deviation between the provisional three-dimensional medical images of two consecutive iterations is fulfilled when a deviation between the provisional three-dimensional medical images of two consecutive iterations falls below the maximum deviation. To determine the deviation the voxel values of two voxels corresponding to one another of the two provisional three-dimensional medical images are subtracted from one another. The deviation then corresponds to a root mean square of the differences determined in such a way. Alternative measures of distance for determining the deviation can be used as an alternative.

The abort criterion can in particular be one of the criteria.

The abort criterion can in particular be the criterion that is the first to be fulfilled. In other words the abort criterion can be fulfilled on fulfillment of any one of the criteria described and the iterations can be aborted.

As an alternative the abort criterion can be a specific one of the three criteria described. In this case the abort criterion is fulfilled when the specific criterion is fulfilled.

As an alternative the abort criterion can be two or all three criteria. The abort criterion is then only fulfilled when both or all three criteria are fulfilled.

FIG. 3 shows a second exemplary embodiment of a method for creating a three-dimensional medical image of an examination object while taking into consideration at least one temporally and/or spatially variable cavitation bubble in the examination object.

The method steps of acquisition REC of the multiplicity of projection images, of determination DET-1 of at least one cavitation bubble projection image, of determination DET-2 of a multiplicity of corrected projection images, of reconstruction DET-3 of the three-dimensional medical image and of provision PROV-1 of the three-dimensional medical image are embodied in a similar way to that described for FIG. 1. In particular the method step of determination DET-2 of the multiplicity of corrected projection images can be embodied in a similar way to that described for FIG. 2.

In this exemplary embodiment the method comprises a method step of determination DET-9 of a spatial environment, in which the at least one cavitation bubble is mapped in the at least one cavitation bubble projection image. In other words, in the method step the environment of the at least one cavitation bubble in the at least one cavitation bubble projection image is determined. The environment in this case is in a spatial relationship to a location or a position of the cavitation bubble. In particular the environment comprises at least one image region in the at least one cavitation bubble projection image, which spatially adjoins the image region that maps the at least one cavitation bubble. The environment is determined as a function of the synchronization between the medical imaging system and the ultrasound system.

As described with regard to FIG. 1, the at least one cavitation bubble projection image can be determined as a function of the temporal synchronization. As a function of the spatial synchronization it can be determined which at least one pixel of the at least one cavitation bubble projection image maps the at least one cavitation bubble. In particular the at least one pixel can be determined, which in accordance with the spatial synchronization maps the location of the focus of the ultrasound pulse in the at least one cavitation bubble projection image. In this case it is assumed that the at least one cavitation bubble is located at the location of the focus. As an alternative the at least one pixel can be determined as a function of the spatial and the temporal synchronization. For this a time interval between the emission of the ultrasound pulse and the acquisition of the at least one cavitation bubble projection image is determined. Subsequently the diffusion of the at least one cavitation bubble in the examination object can be simulated or modeled starting from a point of origin of the at least one cavitation bubble within the time interval. The point of origin can be the location of the focus. As an alternative the point of origin can be in a specific spatial relationship with the location of the focus. The simulation or the model in particular takes account of a material or a material composition or a material property of the examination object. With the simulation or the model a predicted location in the examination object is determined, to which the at least one cavitation bubble has the greatest probability of diffusing in the specific time interval. It can thus be determined through the spatial and temporal synchronization which at least one pixel in the at least one cavitation bubble projection image maps the predicted location.

The environment, in addition to the at least one pixel determined in one of the ways described, comprises pixels of the cavitation bubble projection image that adjoin the at least one pixel. In particular the environment, as a function of an uncertainty of the simulation or of the model or of the focus determined can comprise those pixels, which alternatively with a specific probability map the predicted location of the at least one cavitation bubble or the location of the focus. For this a minimal probability can be defined. The pixels that map the predicted location of the at least one cavitation bubble and/or the location of the focus with a probability that is greater than the minimum probability, can be comprised by the environment.

As an alternative the environment, in addition to the at least one pixel determined in one of the ways described, comprises further pixels depending on their spatial distance from the at least one pixel. A maximum distance can be defined for this. Pixels that are at a distance from the at least one pixel that maps the predicted location of the at least one cavitation bubble or the location of the focus that is greater than the maximum distance can be comprised by the environment.

The minimum probability and the maximum distance can be predetermined or defined manually or automatically.

In versions of embodiments of the present invention, the environment the at least one cavitation bubble in the at least one cavitation bubble projection image is determined as a function of the trajectory of the focus of the ultrasound pulse in the examination object. A multiplicity of cavitation bubbles can be caused or created or arise at different points in time at different locations on the trajectory. The environment of the at least one cavitation bubble then comprises the environment of all cavitation bubbles that exist at the time of acquisition of the at least one cavitation bubble projection image. For this, for each of the cavitation bubbles a sub-environment, as described above, can be determined. A union of the sub-environments of all cavitation bubbles then describes the environment.

In versions of embodiments of the present invention, the environment of the at least one cavitation bubble in the at least one cavitation bubble projection image is determined based on an ultrasound imaging, which represents the at least one cavitation bubble in the examination object. In particular, based on the ultrasound imaging, as an alternative or in addition to the simulation or the model, the predicted location of the at least one cavitation bubble at the time of acquisition of the at least one cavitation bubble projection image can be determined. The predicted location can then be determined, based on the at least one ultrasound image that maps the at least one cavitation bubble.

Then, in the method step of filtering DET-7 of the multiplicity of difference projection images the difference projection image that corresponds to the at least one cavitation bubble projection image, is then multiplied outside the environment with the weighting factor. In other words the pixel values of the pixels that are not comprised by the environment are multiplied by the weighting factor.

In versions of embodiments of the present invention, the pixel values of the pixels that are comprised by the environment can be multiplied by the second weighting factor, as described in the description for FIG. 2.

FIG. 4 shows a third exemplary embodiment of a method for creating a three-dimensional medical image of an examination object while taking into consideration at least one temporally and/or spatially variable cavitation bubble in the examination object.

The method steps of acquisition REC of the multiplicity of projection images, of determination DET-1 of at least one cavitation bubble projection image, of determination DET-2 of a multiplicity of corrected projection images, of reconstruction DET-3 of the three-dimensional medical image and of provision PROV-1 of the three-dimensional medical image are embodied in a similar way to that described for FIG. 1. The method step of determination DET-9 of the spatial environment of the at least one cavitation bubble is embodied in a similar way to that described for FIG. 3.

In this exemplary embodiment the method step of determination DET-2 of the multiplicity of corrected projection images comprises a method step of interpolation DET-10 of the spatial environment of the at least one cavitation bubble as a function of neighboring image regions in the at least one cavitation bubble projection image. In this case the pixel values of the pixels comprised by the environment are replaced by interpolation values. In this case the pixel values can be continuously replaced. The interpolation values depend in this case on the pixel values of the neighboring image regions. The neighboring image regions in this case are the image regions in the at least one cavitation bubble projection image that directly adjoin the environment. The neighboring image regions comprise a subset of the pixels of the cavitation bubble projection image.

The interpolation can be carried out with a standard method. For this, methods for closing up image regions or for correction of error locations in images are known. As an alternative the interpolation or the replacement of the pixel values can be carried out by applying a trained function to the at least one cavitation bubble projection image. Trained functions for closing up gaps or error locations in images or for replacing image regions are known.

Through the interpolation DET-10 the corrected projection image is determined that replaces the at least one cavitation bubble projection image in the multiplicity of corrected projection images.

FIG. 5 shows a second exemplary embodiment of a method step of determination of a multiplicity of corrected projection images.

In particular the method step of determination DET-2 of a multiplicity of corrected projection images in the way described in the description for FIG. 1 can be embodied as described below with regard to FIG. 5.

The method step of determination DET-2 of the multiplicity of corrected projection images comprises a method step of provision PROV-2 of an earlier three-dimensional medical image of the examination object. The earlier three-dimensional medical image maps the examination object at an earlier point in time, i.e. at a point in time before the acquisition of the multiplicity of projection images. The earlier three-dimensional medical image has been reconstructed as a function of a multiplicity of earlier projection images.

In this case the earlier projection images can have been acquired with the same medical imaging system as the multiplicity of projection images.

As an alternative earlier projection images can have been acquired with a different medical imaging system. In this case the different medical imaging system can belong to the same group of medical imaging system as the medical imaging system with which the multiplicity of projection images is acquired. The same group means for example that both medical imaging systems are computed tomography systems. As an alternative the two medical image systems can be C-arm systems for example. The same group thus means that both medical imaging systems are based on the same fundamental technology or method of operating.

As an alternative the two medical imaging systems can belong to different groups of imaging systems. For example the medical imaging system with which the multiplicity of earlier projection images has been acquired can be a magnetic resonance tomography system and the medical imaging system for acquisition of the multiplicity of projection images can be a computed tomography system. As an alternative the medical imaging system with which the multiplicity of earlier projection images has been acquired can be a computed tomography system and the medical imaging system for acquisition of the multiplicity of projection images can be a C-arm system. Any other combinations are possible. In particular the earlier three-dimensional medical image is then processed in such a way that it is similar to the three-dimensional medical image. In particular the range of values of the voxel values of the earlier three-dimensional medical image can be adapted to the voxel values of the three-dimensional medical image.

The method step of determination DET-2 of the multiplicity of corrected projection images moreover comprises a method step of reconstruction DET-4 of a provisional three-dimensional medical image with a standard algorithm as a function of the multiplicity of projection images. This method step is embodied in accordance with the description for the similar method step in FIG. 2.

The method step of determination DET-2 of the multiplicity of corrected projection images moreover comprises a method step of determination DET-11 of a spatial environment of the at least one cavitation bubble in the provisional three-dimensional medical image and in the at least one cavitation bubble projection image as a function of the synchronization.

The environment in this case, as described in the description for FIG. 3, is in a spatial relationship with a position or a location of the at least one cavitation bubble. In particular the environment can comprise at least one image region in the at least one cavitation bubble projection image or in the three-dimensional medical image that adjoins the image region that maps the at least one cavitation bubble.

The environment of the at least one cavitation bubble in the at least one cavitation bubble projection image is embodied as described in the description for the corresponding method step of determination DET-9 of the spatial environment in FIG. 3.

The environment of the at least one cavitation bubble in the provisional three-dimensional medical image can be determined in a similar way. It is known where in the examination object the focus of the ultrasound pulse is positioned. Because of the spatial synchronization the corresponding position or the location of the focus in the provisional three-dimensional medical image can be derived from this. In other words, as a function of the spatial synchronization the at least one voxel of the provisional three-dimensional medical image can be determined that corresponds to the position or the location of the focus in the examination object.

In a simplified assumption it can be assumed that the at least one cavitation bubble at this position has been caused or created by the ultrasound pulse and is mapped there. The environment can then comprise further voxels adjoining or neighboring the at least one voxel positioned at the location of the focus. In this case the further voxels, as a function of a probability that as an alternative or in addition they map the at least one cavitation bubble can be comprised by the environment. As an alternative or in addition the voxel, as a function of its spatial distance from the at least one voxel, can be comprised by the environment. The voxels comprised by the environment can be determined in a similar way to that described in accordance with the description for FIG. 3.

In addition it can be simulated or modeled via a simulation or a model how the at least one cavitation bubble diffuses through the examination object. In this case, based on the temporal synchronization, it can be determined at which locations or positions in the examination object the at least one cavitation bubble probably was during the acquisition of the multiplicity of projection images. Based on the spatial synchronization, the voxels in the provisional three-dimensional medical image that map these predicted locations in the examination object can be determined from this. These voxels can then be comprised by the environment. Moreover voxels that adjoin these voxels can be comprised by the environment in accordance with the criteria described above (probability or uncertainty and/or distance).

As an alternative or in addition the predicted location or the predicted position of the at least one cavitation bubble can be determined with ultrasound imaging, as described in the description for FIG. 3.

In particular, as described in the description for FIG. 3, a trajectory of the focus of the ultrasound pulse in the examination object can be taken into consideration in the determination of the environment in the provisional three-dimensional medical image. In this case the environment can comprise at least the voxels that lie on the trajectory of the focus.

The method step of determination DET-2 of the multiplicity of corrected projection images moreover comprises a method step of registration DET-12 of the provisional three-dimensional medical image with the earlier three-dimensional medical image. During registration DET-12 the earlier three-dimensional medical image is registered via an affine transformation with the provisional three-dimensional medical image. In this case a one-to-one correspondence between the voxels of the earlier three-dimensional medical image and of the provisional three-dimensional medical image is determined. In other words pairs of voxels that correspond to one another are determined in the two images in each case. Two voxels corresponding to one another in this case map the same part of the examination object.

The method step of determination DET-2 of the multiplicity of corrected projection images moreover comprises a method step of replacement DET-13 of the environment of the at least one cavitation bubble in the provisional three-dimensional medical image by the corresponding environment in the earlier three-dimensional medical image. In this case the voxel values of the voxels comprised by the environment of the at least one cavitation bubble in the provisional three-dimensional medical image are replaced by the voxel values of the corresponding voxels in the earlier three-dimensional medical image.

The method step of determination DET-2 of the multiplicity of corrected projection images moreover comprises a method step of determination DET-14 of a multiplicity of provisional projection images by forward projection of the provisional three-dimensional medical image. The provisional projection images are determined in such a way that each provisional projection image is assigned or corresponds to precisely one projection image. Two projection images corresponding or assigned to one another map the examination object from the same angle in this case. In particular in two projection images assigned or corresponding to one another, each pixel of the provisional projection image is assigned a pixel of the projection image. Pixels assigned to one another map the same part of the examination object from the same angle ab.

The method step of determination DET-2 of the multiplicity of corrected projection images moreover comprises a method step of replacement DET-15 of the environment of the at least one cavitation bubble in the at least one cavitation bubble projection image by the corresponding region from the assigned provisional projection image. In this case the pixel values of the pixels comprised by the environment of the at least one cavitation bubble in the cavitation bubble projection image are replaced by the pixel values of the pixels assigned to the environment of the provisional projection image assigned to the cavitation bubble projection image. In this way the corrected projection image corresponding to the cavitation bubble projection image is determined. In other words the cavitation bubble projection image, in which the environment of the at least one cavitation bubble was replaced is the corrected projection image. The corrected projection image is then comprised by the multiplicity of corrected projection images.

FIG. 6 shows a system SYS for creating a three-dimensional medical image of an examination object while taking into consideration at least one temporally and/or spatially variable cavitation bubble in the examination object.

The system SYS shown for creating a three-dimensional medical image of an examination object while taking into consideration at least one temporally and/or spatially variable cavitation bubble in the examination object is embodied to carry out an inventive method for creating a three-dimensional medical image of an examination object while taking into consideration at least one temporally and/or spatially variable cavitation bubble in the examination object. The system SYS comprises an interface SYS.IF, a processing unit SYS.CU and a memory unit SYS.MU.

The system SYS can in particular be a computer, a microcontroller or an integrated circuit (IC). As an alternative the system SYS can be a real or virtual computer network (a technical term for a real computer network is "cluster", a technical term for a virtual computer network is "cloud"). The system SYS can be embodied as a virtual system, which is executed on a computer or real computer network or a virtual computer network (a technical term is "virtualization").

The interface SYS.IF can be a hardware or software interface (for example a PCI bus, USB or Firewire). The processing unit SYS.CU can comprise hardware and/or software components, for example a microprocessor or what is known as an FPGA (Field Programmable Gate Array). The memory unit SYS.MU can be embodied as non-permanent working memory (Random Access Memory, RAM) or as permanent mass storage (hard disk, USB stick, SD card, Solid State Disk (SSD)).

The interface SYS.IF can in particular comprise a multiplicity of sub-interfaces, which carry out various method steps of the respective inventive method. In other words the interface SYS.IF can be embodied as a multiplicity of interfaces SYS.IF. The processing unit SYS.CU can in particular comprise a multiplicity of sub-processing units, which carry out various method steps of the respective inventive method. In other words the processing unit SYS.CU can be embodied as a multiplicity of processing units SYS.CU.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

Where this has not occurred explicitly but is meaningful in the sense of the present invention, individual exemplary embodiments, individual of their subaspects or features can be combined with one another or exchanged for one another without departing from the framework of the current invention. Advantages of the present invention described with regard to one exemplary embodiment also apply, without this being explicitly stated, where transferrable, to other exemplary embodiments.

What is claimed is:

1. A computer-implemented method for creating a three-dimensional medical image of an examination object taking into consideration at least one cavitation bubble in the examination object, the at least one cavitation bubble including at least one of at least one temporally variable cavitation bubble or at least one spatially variable cavitation bubble, and the at least one cavitation bubble being caused by at least one ultrasound pulse emitted into the examination object by an ultrasound system, wherein the method comprises:
    acquiring a multiplicity of projection images of the examination object with a medical imaging system, the medical imaging system being in synchronization with the ultrasound system;
    determining at least one cavitation bubble projection image from the multiplicity of projection images as a function of the synchronization, the at least one cavitation bubble projection image being a projection image of the multiplicity of projection images in which the at least one cavitation bubble is mapped;
    determining a multiplicity of corrected projection images, wherein the at least one cavitation bubble projection image, in the multiplicity of projection images, is replaced by a corrected projection image;
    reconstructing the three-dimensional medical image as a function of the multiplicity of corrected projection images; and
    provisioning the three-dimensional medical image.

2. The computer-implemented method as claimed in claim 1, wherein the determining of the multiplicity of corrected projection images comprises:
    reconstructing a provisional three-dimensional medical image with a standard algorithm as a function of the multiplicity of projection images;
    determining a multiplicity of provisional projection images by forward projection of the provisional three-dimensional medical image, wherein one projection image corresponds to each of the provisional projection images;
    determining a multiplicity of difference projection images by subtraction of one or more projection images from a corresponding provisional projection image;
    filtering the multiplicity of difference projection images, wherein at least those difference projection images that do not map the at least one cavitation bubble are weighted; and
    adding one or more projection images to a corresponding filtered difference projection image in each case, to determine the multiplicity of corrected projection images.

3. The computer-implemented method as claimed in claim 2, wherein
    the reconstructing of the provisional three-dimensional medical image, the determining of the multiplicity of provisional projection images, the determining of the multiplicity of difference projection images, the filtering of the multiplicity of difference projection images, and the adding of the one or more projection images to the corresponding filtered difference projection image, are repeated iteratively until an abort criterion is fulfilled, and
    in a second and further iterations, the provisional three-dimensional medical image is determined as a function of the multiplicity of corrected projection images determined in a previous iteration.

4. The computer-implemented method as claimed in claim 3, wherein the abort criterion includes at least one of
    a maximum number of iterations,
    a maximum deviation between the provisional projection images of two consecutive iterations, or
    a maximum deviation between the provisional three-dimensional medical images of two consecutive iterations.

5. The computer-implemented method as claimed in claim 4, wherein
    at least those difference projection images that do not map the at least one cavitation bubble are weighted by a weighting factor,
    the weighting factor is greater than or equal to 0, and
    the weighting factor is less than 1.

6. The computer-implemented method as claimed in claim 4, further comprising:
    determining a spatial environment in which the at least one cavitation bubble is mapped in the at least one cavitation bubble projection image, as a function of the synchronization, wherein
        the filtering of the multiplicity of difference projection images includes weighting, outside the spatial environment of the at least one cavitation bubble, a difference projection image corresponding to the at least one cavitation bubble projection image.

7. The computer-implemented method as claimed in claim 3, wherein
    at least those difference projection images that do not map the at least one cavitation bubble are weighted by a weighting factor,
    the weighting factor is greater than or equal to 0, and
    the weighting factor is less than 1.

8. The computer-implemented method as claimed in claim 3, further comprising:
    determining a spatial environment in which the at least one cavitation bubble is mapped in the at least one cavitation bubble projection image, as a function of the synchronization, wherein
        the filtering of the multiplicity of difference projection images includes weighting, outside the spatial environment of the at least one cavitation bubble, a difference projection image corresponding to the at least one cavitation bubble projection image.

9. The computer-implemented method as claimed in claim 2, wherein
    at least those difference projection images that do not map the at least one cavitation bubble are weighted by a weighting factor,
    the weighting factor is greater than or equal to 0, and
    the weighting factor is less than 1.

10. The computer-implemented method as claimed in claim 9, further comprising:
    determining a spatial environment in which the at least one cavitation bubble is mapped in the at least one cavitation bubble projection image, as a function of the synchronization, wherein
        the filtering of the multiplicity of difference projection images includes weighting, outside the spatial environment of the at least one cavitation bubble, a difference projection image corresponding to the at least one cavitation bubble projection image.

11. The computer-implemented method as claimed in claim 2, further comprising:
    determining a spatial environment in which the at least one cavitation bubble is mapped in the at least one cavitation bubble projection image, as a function of the synchronization, wherein
        the filtering of the multiplicity of difference projection images includes weighting, outside the spatial environment of the at least one cavitation bubble, a difference projection image corresponding to the at least one cavitation bubble projection image.

12. The computer-implemented method as claimed in claim 11, wherein the spatial environment of the at least one cavitation bubble in the at least one cavitation bubble projection image is determined as at least one of a function of a point in time of emission of the ultrasound pulse, as a function of a trajectory of a focus of the ultrasound pulse in the examination object, or based on ultrasound imaging, which represents the at least one cavitation bubble in the examination object.

13. The computer-implemented method as claimed in claim 1, wherein the determining of the multiplicity of corrected projection images comprises:
    determining a spatial environment in which the at least one cavitation bubble is mapped in the at least one cavitation bubble projection image, as a function of the synchronization; and
    interpolating the spatial environment of the at least one cavitation bubble as a function of neighboring image regions in the at least one cavitation bubble projection image.

14. The computer-implemented method as claimed in claim 13, wherein the spatial environment of the at least one cavitation bubble in the at least one cavitation bubble projection image is determined as at least one of a function of a point in time of emission of the ultrasound pulse, as a function of a trajectory of a focus of the ultrasound pulse in the examination object, or based on ultrasound imaging, which represents the at least one cavitation bubble in the examination object.

15. The computer-implemented method as claimed in claim 1, wherein the determining of the multiplicity of corrected projection images comprises:
    provisioning of an earlier three-dimensional medical image of the examination object;
    reconstructing a provisional three-dimensional medical image with a standard algorithm as a function of the multiplicity of projection images;
    determining a spatial environment of the at least one cavitation bubble in the provisional three-dimensional medical image and in the at least one cavitation bubble projection image as a function of the synchronization;
    registering the provisional three-dimensional medical image with the earlier three-dimensional medical image;
    replacing the spatial environment of the at least one cavitation bubble in the provisional three-dimensional medical image by a corresponding environment in the earlier three-dimensional medical image;
    determining a multiplicity of provisional projection images by forward projection of the provisional three-dimensional medical image, wherein each of the provisional projection images is assigned one projection image; and
    replacing a spatial environment of the at least one cavitation bubble in the at least one cavitation bubble projection image by a corresponding region from an assigned provisional projection image.

16. The computer-implemented method as claimed in claim 1, wherein the ultrasound system and the medical imaging system are synchronized with one another at least one of temporally or spatially.

17. The computer-implemented method as claimed in claim 1, wherein at least one of
    the ultrasound system is a histotripsy system, or
    the medical imaging system is an x-ray system.

18. A system for creating a three-dimensional medical image of an examination object taking into consideration at least one cavitation bubble in the examination object, the at least one cavitation bubble including at least one of at least one temporally variable cavitation bubble or at least one spatially variable cavitation bubble, and the at least one cavitation bubble caused by at least one ultrasound pulse emitted by an ultrasound system into the examination object, wherein the system comprises:
    an interface and at least one processor, at least one of the interface or the at least one processor configured to acquire a multiplicity of projection images of the examination object with a medical imaging system, the medical imaging system in synchronization with the ultrasound system,
    wherein the at least one processor is configured to
        determine at least one cavitation bubble projection image from the multiplicity of projection images as a function of the synchronization, the at least one cavitation bubble projection image being a projection image of the multiplicity of projection images in which the at least one cavitation bubble is mapped,
        determine a multiplicity of corrected projection images, wherein the at least one cavitation bubble projection image, in the multiplicity of projection images, is replaced by a corresponding corrected projection image, and
        reconstruct the three-dimensional medical image as a function of the multiplicity of corrected projection images, and
    wherein the interface is configured to provision the three-dimensional medical image.

19. A non-transitory computer program product having a computer program that is loadable into a memory of a system, the computer program including program sections that, when executed by the system, cause the system to perform the method as claimed in claim 1.

20. A non-transitory computer-readable storage medium storing program sections that, when executed by a determination system, cause the determination system to perform the method of claim 1.

* * * * *